United States Patent [19]

Cazenave et al.

[11] Patent Number: 5,225,420
[45] Date of Patent: Jul. 6, 1993

[54] USE OF TETRAHYDROTHIENOPYRIDINE DERIVATIVES AS ANGIOGENESIS INHIBITORS

[75] Inventors: Jean-Pierre Cazenave, Lampertheim; Jean-Marc Herbert, Plaisance du Touch, both of France

[73] Assignee: Elf-Sanofi, Paris, France

[21] Appl. No.: 833,765

[22] Filed: Feb. 11, 1992

[30] Foreign Application Priority Data

Feb. 14, 1991 [FR] France .................. 91 01783

[51] Int. Cl.$^5$ .................... A61K 31/47
[52] U.S. Cl. ..................... 514/310
[58] Field of Search ................. 514/310

[56] References Cited

FOREIGN PATENT DOCUMENTS 0099802 2/1984 European Pat. Off. .
0281459 9/1988 European Pat. Off. .

OTHER PUBLICATIONS

R. A. Fraser et al., "Role of Mast Cells in Experimental Tumour Antiogenesis," Ciba Foundation Symposium 100, pp. 120-131, 1983.

R. L. Barnhill et al., et al., "Biochemical Modulation of Angiogenesis in the Chorioallantoic Membrane of the Chick Embryo," J. Invest. Dermatol., vol. 81, No. 6, pp. 485-488, 1983.

R. Feliste et al., "Broad Spectrum Anti-Platelet Activity of Ticlopidine and PCR 4099 Involves the Suppression of the Effects of Released ADP," Thromb. Res., vol. 48, No. 4, pp. 403-415, 1987.

J. P. Maffrand et al., "Nouvelles Therapeutiques Antiagregantes," Sang Thromb. Vaiss., vol. 2, No. 4, pp. 175-177, 1990.

Primary Examiner—S. J. Friedman
Attorney, Agent, or Firm—Wegner, Cantor, Mueller & Player

[57] ABSTRACT

The invention relates to the use of compounds of the formula

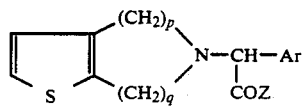

in which p is 2 and q is 1 or p is q and q is 2; Ar represents an optionally substituted phenyl, and Z represents $NR_1R_2$ in which $R_1$ and $R_2$, which may be identical or different, represent H or optionally substituted alkyl or, with the nitrogen atom, form a saturated heterocycle, or Z represents OR in which R is H or optionally substituted alkyl, or their addition salts, in the form of pure enantiomer or of mixtures thereof, for administration in a human patient for preventing or treating pathologies involving or dependent upon a neovascularization.

4 Claims, No Drawings

USE OF TETRAHYDROTHIENOPYRIDINE DERIVATIVES AS ANGIOGENESIS INHIBITORS

The present invention relates to the use of tetrahydrothienopyridine derivatives for administration in a human patient for preventing or treating pathologies involving or dependent upon a neovascularisation, and in particular retinopathies, rheumatoid arthritis, psoriasis, some cancerous tumours, angiomas, Kaposi's syndrome and the complications of AIDS, cutaneous keloids, the complications of burns, graft rejections and endometriosis.

These compounds are effective angiogenesis inhibitors.

The compounds which are usable according to the invention are those corresponding to the formula

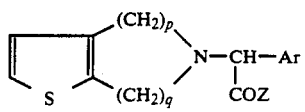   I in which
  p is 2 and q is 1 or p is 1 and q is 2; Ar represents a phenyl, unsubstituted or bearing one or more substituents chosen from halo, $C_1$ to $C_3$ alkyl, $C_1$ to $C_3$ alkoxy, nitro or trifluoromethyl; and
  Z represents $NR_1R_2$ in which $R_1$ and $R_2$, which may be identical or different, represent H or $C_1$ to $C_4$ alkyl optional substituted with $NR_3R_4$, pyridyl or with phenyl, unsubstituted or substituted with halo, $C_1$ to $C_3$ alkyl, $C_1$ to $C_3$ alkoxy, nitro or trifluoromethyl, or, with the nitrogen atom, form a saturated heterocycle, or Z represents OR in which R is H or $C_1$ to $C_6$ alkyl optionally substituted with OH or $NR'_3R'_4$, and $R_3$, $R'_3$, $R_4$ and $R'_4$ each represent H or $C_1$ to $C_4$ alkyl, or, with the nitrogen atom, form a saturated heterocycle,
or a salt thereof with pharmaceutically acceptable inorganic or organic acid or base.

Saturated heterocycle is understood to mean piperidino, pyrrolidinyl, morpholino or 1-piperazinyl, and alkyl and alkoxy to mean the straight-chain or branched groups.

These compounds contain at least one asymmetric carbon, and the pure enantiomers as well as mixtures thereof in any proportions, and in particular the racemates, are usable according to the invention.

The compounds of formula I in which Ar represents a phenyl ring substituted with a halogen atom and, better still, an ortho-chlorinated phenyl ring, and Z represents methoxy or ethoxy are preferred. Among these compounds, the laevorotatory isomers, of absolute configuration S defined according to the sequence rule procedure, are preferred.

These compounds, a number of which are known and are, in particular, described in EP-A-0,099,802 and EP-A-0,281,459, may be prepared in a conventional manner by the action of a phenylacetic derivative of formula

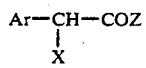

in which X represents Cl or Br on 4,5,6,7-tetrahydrothieno[3,2-c]pyridine, a known compound of formula

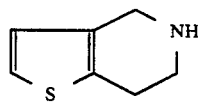   III or its known isomer of formula IV

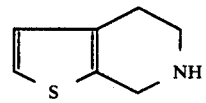   IV in a protic polar solvent such as an alcohol or an aprotic polar solvent such as acetone or dimethylformamide, in the presence of an inorganic or organic base to neutralise the acid formed.

In the case where Z is OH, the substitution of the heterocyclic nitrogen is generally performed with a compound of formula II in which Z represents an alkoxy, and the ester obtained will be hydrolysed in a conventional manner in an aqueous medium, preferably in the presence of a base; from the alkyl esters, it is also possible to prepare the compounds in which Z represents $NR_1R_2$ or substituted alkyl esters, by methods known per se.

The enantiomers of the compounds of formula I may be obtained in a conventional manner, either from the racemic mixture by recrystallisations of a salt with an optically active acid such as one of the enantiomers of 10-camphorsulphonic acid or of tartaric acid, or by reacting only one of the enantiomers of the compound of formula II with the compounds of formula III or IV under non-racemising conditions.

The pharmaceutical compositions according to the present invention, comprising the compounds of formula I or their salts in combination with compatible usual excipients, will be prepared according to the usual pharmaceutical formulation methods so that they can be administered orally, transmucosally or by injection.

The invention also comprises a pharmaceutical composition containing the laevorotatory isomer of methyl alpha-(4,5,6,7-tetrahydrothieno[3,2-c]pyrid-5-yl)-alpha-(2-chlorophenyl)acetate (compound No. 4 of Table I) and its pharmaceutically acceptable organic or inorganic salts. This compound was described and found inactive as platelet aggregation inhibitor in EP-A-0 281,459. No other pharmacological activity was known before.

The unit and daily doses will depend on the intrinsic activity of the active principle and will match the type and intensity of the pathology to be prevented or treated, as well as the patient's age and weight. In adults, for oral administration, the unit dose can be between 5 mg and 500 mg.

When one of the enantiomers is markedly more active than the other one without any simultaneous increase in toxicity, this enantiomer will preferably be used, pure or in combination with less than 10% of its homologue.

It is known, in addition, from Patents EP-0,099,802 and EP-0,281,459 that some of the compounds of the formula I also have platelet aggregation-inhibiting activity, the intensity of which is dependent on the configuration of the molecule on the asymmetric carbon atom bound to the heterocyclic nitrogen atom, and it is preferable to use the enantiomers of the products possessing only a slight associated aggregation inhibiting activity for preparing the angiogenesis inhibiting pharmaceutical compositions of the invention.

Pharmacological tests demonstrating the angiogenesis-inhibiting activity of representative compounds of the invention are described below.

In vitro test:

A nutrient medium (Dulbecco's modified Eagle medium-DMEM), supplemented with fetal calf serum (concentration: 5% V/V) and containing glutamine (4 mM), penicillin (100 U/ml) and streptomycin sulphate (100 μg/ml), is introduced into 1-ml wells and innoculated with bovine cerebral cortex capillary endothelial cells ($20 \times 10^3$ cells/ml), isolated and cultured as described by D. Gospodarowicz et al. in J. Cell. Physiol. 127, p. 121–136 (1986).

As soon as cell adhesion has taken place, 1 ng/ml of recombinant bovine basic fibroblast growth factor (rb-FGF), marketed by Amersham, a known factor for the stimulation of angiogenesis in vivo, is added, followed by the test solutions.

Cell counting is performed 5 days after the addition of 20 μl of a solution of the test products in dimethyl sulphoxide such that their final concentration in the medium is between $10^{-4}$ and $10^{-8}$ M; the control wells receive 20 μl of solvent.

From the results obtained for several concentrations of each of the test products, the concentration at which the latter produce a 50% inhibition of cell proliferation is calculated in a conventional manner.

The results obtained appear in Table I.

In vivo test:

H. F. Dvorak et al. have shown that fibrin gels induce an angiogenic response in vivo in rats.

Their technique, described in Laboratory Investigation 57 (6) 673–686 (1987), was used to demonstrate the angiogenesis-inhibiting activity of the compounds of the invention.

Perforated Plexiglas chambers containing a fibrin gel, obtained by polymerisation of rat fibrinogen in the presence of thrombin, are implanted subcutaneously in rats. The fibrin is invaded sequentially and organised by different types of cells, such as leukocytes, macrophages, fibroblasts and endothelial cells, leading to the formation of a neovascularised granulation tissue.

The test products, suspended in absolute alcohol and 5% gum arabic (10 ml/kg), are administered orally to the rats at doses of 5 and 25 mg/kg/day for the compounds of Examples 3 and 4, for 5 days before implantation and up to the time of removal of the chambers. After 14 days, a granulation outgrowth is formed, and the chambers are removed in order to observe the height of the granulation outgrowth anchored in the matrix and the quantity of newly-formed vessels which have appeared.

In another experiment to study the regression of the angiogenesis, the chambers are implanted in untreated rats and the daily administration of the test products is begun only after 14 days; the appearance of the outgrowth formed is observed after 8 and 14 days of treatment.

It was found in both series of experiments that the compound No. 3 is markedly more active than its homologue, the compound No. 4, when they are administered at a dose of 25 mg/kg/day, and the compound No. 3 is still very active at a dose of 5 mg/kg/day.

The inhibition of the angiogenic response was evaluated by:

(i) the height and diameter of the granulation outgrowths, (ii) the number of newly-formed vessels per outgrowth and their localisation, (iii) the quality of the granulation tissue.

The height of the granulation outgrowths is inhibited by 50% after administration of the compound of Example 3 and by 30% afteradministration of that of Example 4 (25 mg/kg/day). The former compound remains effective at 5 mg/kg/day (50% inhibition) in contrast to the latter compound (5 mg/kg/day). The number of newly-formed vessels per outgrowth is significantly lowered by 90% with the former compound (25 mg/kg/day) and by 60% with the latter compound (25 mg/kg/day), and 50% in the presence of the former compound at 5 mg/kg/day.

The granulation tissue is seen to be more loose-textured and disorganised after treatment with the compound of Example 3.

TABLE I

| Compound No. | Formula | isomer | M.p.° (salt) | IC$_{50}$ (nM) |
|---|---|---|---|---|
| 1 | [structure: thiophene-fused ring with N–CH(COOH)–phenyl-Cl] | + | 205° C. HCl | 600 |
| 2 | [structure: thiophene-fused ring with N–CH(COOCH$_3$)–phenyl-Cl] | ± | 140° C. HCl | 2.3 |
| 3 | [structure: thiophene-fused ring with N–CH(COOCH$_3$)–phenyl-Cl] | + | 178° C. H$_2$SO$_4$ | 0.8 |

TABLE I-continued

| Compound No. | Formula | isomer | M.p.° (salt) | IC$_{50}$ (nM) |
|---|---|---|---|---|
| 4 | thieno-tetrahydropyridine–N–CH(2-Cl-C$_6$H$_4$)–COOCH$_3$ | — | 178° C. H$_2$SO$_4$ | 3.7 |
| 5 | thieno-tetrahydropyridine–N–CH(2-Cl-C$_6$H$_4$)–COOC$_2$H$_5$ | ± | 180° C. HBr | 70 |
| 6 | thieno-tetrahydropyridine–N–CH(2-Cl-C$_6$H$_4$)–COOC$_4$H$_9$ | ± | 155° C. H$_2$SO$_4$ | 220 |
| 7 | thieno-tetrahydropyridine–N–CH(2-Cl-C$_6$H$_4$)–CON(CH$_3$)$_2$ | ± | 95° C. base | 80 |
| 8 | thieno-tetrahydropyridine–N–CH(2-Cl-C$_6$H$_4$)–CONHCH$_3$ | ± | 137° C. base | 50 |
| 9 | thieno-tetrahydropyridine–N–CH(2-Cl-C$_6$H$_4$)–CON(pyrrolidinyl) | ± | 130° C. base | 320 |
| 10 | thieno-tetrahydropyridine–N–CH(2-Cl-C$_6$H$_4$)–COO(CH$_2$)$_2$–N(morpholino) | ± | 203° C. (COOH)$_2$ | 20 |
| 11 | thieno-tetrahydropyridine–N–CH(2-Cl-C$_6$H$_4$)–CONH(CH$_2$)$_3$N(CH$_3$)$_2$ | ± | 210° C. 2 HCl | 80 |

TABLE I-continued

| Compound No. | Formula | isomer | M.p.° (salt) | IC$_{50}$ (nM) |
|---|---|---|---|---|
| 12 | thieno[3,2-c]tetrahydropyridine–N–CH(2-Cl-C$_6$H$_4$)–CONHCH$_2$-(2-pyridyl) | ± | 122° C. base | 30 |
| 13 | thieno[3,2-c]tetrahydropyridine–N–CH(2-Cl-C$_6$H$_4$)–CONHCH$_2$-(2-Cl-C$_6$H$_4$) | ± | 116° C. base | 1.9 |
| 14 | thieno[3,2-c]tetrahydropyridine–N–CH(3-Cl-C$_6$H$_4$)–COOCH$_3$ | ± | 186° C. HCl | 60 |
| 15 | thieno[3,2-c]tetrahydropyridine–N–CH(4-Cl-C$_6$H$_4$)–COOCH$_3$ | ± | 202° C. HCl | 360 |
| 16 | thieno[3,2-c]tetrahydropyridine–N–CH(2-F-C$_6$H$_4$)–COOCH$_3$ | ± | 100° C. HCl | 110 |
| 17 | thieno[3,2-c]tetrahydropyridine–N–CH(2-CH$_3$-C$_6$H$_4$)–COOC$_2$H$_5$ | ± | 188° C. H$_2$SO$_4$ | 110 |
| 18 | thieno[3,2-c]tetrahydropyridine–N–CH(C$_6$H$_5$)–COOCH$_3$ | ± | 200° C. HCl | 410 |
| 19 | thieno[3,2-c]tetrahydropyridine–N–CH(COOCH$_3$)–(2-Cl-C$_6$H$_4$) | ± | 150° C. HCl | 120 |

We claim:

1. A method of preventing or treating pathologies involving or dependent upon a neovascularisation in a human patient, comprising administration to a human patient of an effective amount of a compound of the formula

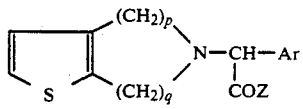

in which
p is 2 and q is 1 or p is 1 and q is 2;
Ar represents a phenyl, unsubstituted or bearing one or more substituents chosen from halo, $C_1$ to $C_3$ alkyl, $C_1$ to $C_3$ alkoxy, nitro or trifluoromethyl; and
Z represents $NR_1R_2$ in which $R_1$ and $R_2$, which may be identical or different, represent H or $C_1$ to $C_4$ alkyl optional substituted with $NR_3R_4$ or with phenyl, unsubstituted or substituted with halo, $C_1$ to $C_3$ alkyl, $C_1$ to $C_3$ alkoxy, nitro or trifluoromethyl; or Z represents OR in which R is H or $C_1$ to $C_6$ alkyl unsubstituted or substituted with OH or $NR'_3R'_4$,
and $R_3$, $R'_3$, $R_4$ and $R'_4$ each represent H or $C_1$ to $C_4$ alkyl,
or its salts thereof with a pharmaceutically acceptable inorganic or organic acid or base wherein the compound of formula I is a substantially pure enantiomer or a mixture of enantiomers in any proportions.

2. The method of claim 1, wherein said compound is of formula I in which Ar represents a phenyl substituted with a halogen atom, or a salt thereof.

3. The method of claim 1, wherein said compound is of formula I in which Ar represents an ortho-chlorophenyl and Z represents a $C_1$ or $C_2$ alkoxy group, or a salt thereof.

4. The method of claim 1, wherein said compound is the laevorotatory isomer of the compound of formula

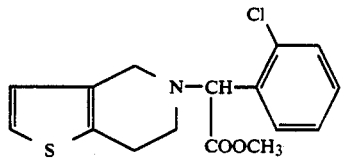

or a salt thereof.

* * * * *